US010064891B2

(12) United States Patent
Meledandri et al.

(10) Patent No.: US 10,064,891 B2
(45) Date of Patent: Sep. 4, 2018

(54) ASSEMBLY OF MICELLE AGGREGATES OF SURFACTANT MICELLES AND SILVER NANOPARTICLES AND USE AS ANTIBACTERIAL AGENT

(71) Applicant: Otago Innovation Limited, Dunedin (NZ)

(72) Inventors: Carla Joy Meledandri, Dunedin (NZ); Donald Royden Schwass, Dunedin (NZ)

(73) Assignee: OTAGO INNOVATION LIMITED, Dunedin (NZ)

( * ) Notice: Subject to any disclaimer, the term of this patent is extended or adjusted under 35 U.S.C. 154(b) by 0 days.

(21) Appl. No.: 14/763,108

(22) PCT Filed: Jan. 24, 2014

(86) PCT No.: PCT/NZ2014/000006
§ 371 (c)(1),
(2) Date: Jul. 23, 2015

(87) PCT Pub. No.: WO2014/116121
PCT Pub. Date: Jul. 31, 2014

(65) Prior Publication Data
US 2015/0366904 A1     Dec. 24, 2015

Related U.S. Application Data

(60) Provisional application No. 61/756,681, filed on Jan. 25, 2013.

(51) Int. Cl.
*A61K 33/38*        (2006.01)
*A61K 47/20*        (2006.01)
(Continued)

(52) U.S. Cl.
CPC .............. *A61K 33/38* (2013.01); *A61C 19/06* (2013.01); *A61K 9/0063* (2013.01);
(Continued)

(58) Field of Classification Search
CPC .... A61K 33/38; A61K 9/0063; A61K 9/1075; A61K 47/20; A61K 9/14; A61C 19/06; A61N 1/30; A61N 1/205; Y02A 50/473
(Continued)

(56) References Cited

U.S. PATENT DOCUMENTS 6,660,058 B1 * 12/2003 Oh .................. B22F 1/0018
                                                       75/351
7,374,599 B1    5/2008 Shelnutt et al.
(Continued)

FOREIGN PATENT DOCUMENTS

WO    WO 2006085975 A2 *  8/2006

OTHER PUBLICATIONS

Dong et al., "Crystallization of Silver Carboxylates from Sodium Carboxylate Mixtures", Langmuir 2007, 23, 7963-7971.*
(Continued)

*Primary Examiner* — Daniel S Metzmaier
(74) *Attorney, Agent, or Firm* — Knobbe Martens Olson & Bear LLP

(57) ABSTRACT

An assembly of micelle aggregates, wherein each aggregate comprises micelles of an anionic surfactant and nano-sized particles of metallic silver. A product comprising such assemblies for use in treating or preventing bacterial infections.

16 Claims, 6 Drawing Sheets

(51) Int. Cl.
- *A61K 9/107* (2006.01)
- *A61K 9/00* (2006.01)
- *A61N 1/30* (2006.01)
- *A61C 19/06* (2006.01)
- *A61K 9/14* (2006.01)
- *A01N 1/02* (2006.01)
- *A61N 1/20* (2006.01)

(52) U.S. Cl.
CPC .............. *A61K 9/1075* (2013.01); *A61K 9/14* (2013.01); *A61K 47/20* (2013.01); *A61N 1/30* (2013.01); *A61N 1/205* (2013.01); *Y02A 50/473* (2018.01)

(58) Field of Classification Search
USPC ............ 516/97; 424/417, 420, 618; 514/495
See application file for complete search history.

(56) References Cited

U.S. PATENT DOCUMENTS

| | | | |
|---|---|---|---|
| 8,883,122 B2* | 11/2014 | Brougham | A61K 41/0052 424/9.1 |
| 9,243,141 B1* | 1/2016 | Farrugia | C08L 67/02 |
| 2009/0013825 A1 | 1/2009 | Rahman | |
| 2011/0293941 A1* | 12/2011 | Chaumonnot | C01B 37/00 428/404 |
| 2012/0282182 A1* | 11/2012 | Brougham | A61K 41/0052 424/9.1 |
| 2012/0292579 A1* | 11/2012 | Sureshkumar | B82Y 30/00 252/582 |

OTHER PUBLICATIONS

Chaudhari, Vijay R. et al., "Micelle assisted morphological evolution of silver nanoparticles" Colloids and Surfaces A: Physicochem. Eng. Aspects, 2007, pp. 475-780, vol. 301.

López-Miranda, A. et al., "Silver nanoparticles synthesis in aqueous solutions using sulfite as reducing agent and sodium dodecyl sulfate as stabilizer" J Nanopart Res, 2012, pp. 1-11, vol. 14, No. 1101.

Rao, Feng et al., "Synthesis and Characterization of Silver Nanorods in Aqueous Sodium Dodecylsulfate Solutions" Journal of Dispersion Science and Technology, 2012, pp. 799-804, vol. 33.

Supplementary European Search Report for EP 14743761 dated Sep. 20, 2016.

Al-Thabaiti, Shaeel Ahmed et al., "Formation and characterization of surfactant stabilized silver nanoparticles: A kinetic study" Colloids and Surfaces B: Biointerfaces, 2008, pp. 230-237, vol. 67.

Qiao, Yan et al., "Metal-Driven Viscoelastic Wormlike Micelle in Anionic/Zwitterionic Surfactant Systems and Template-Directed Synthesis of Dendritic Silver Nanostructures" Langmuir, 2011, pp. 1718-1723, vol. 27, No. 5.

International Search Report for PCT/NZ2014/000006 dated May 15, 2014.

* cited by examiner

ASSEMBLY OF MICELLE AGGREGATES OF SURFACTANT MICELLES AND SILVER NANOPARTICLES AND USE AS ANTIBACTERIAL AGENT

CROSS REFERENCE TO RELATED APPLICATIONS

This application is a U.S. National Phase Application of PCT International Application Number PCT/NZ2014/000006, filed on Jan. 24, 2014, designating the United States of America and published in the English language, which is an International Application of and claims the benefit of priority to U.S. Provisional Application No. 61/756,681, filed on Jan. 25, 2013. The disclosures of the above-referenced applications are hereby expressly incorporated by reference in their entireties.

TECHNICAL FIELD

The invention relates to an assembly of surfactant molecules and silver nanoparticles. In particular, the invention relates to an assembly of aggregated micelles of an anionic surfactant and nano-sized metallic silver particles. The invention also relates to a method for preparing the assemblies of the invention. The invention further relates to the use of an aqueous dispersion of such assemblies for treating or preventing bacterial infections, particularly bacterial infections of human teeth.

BACKGROUND OF THE INVENTION

The expanding capabilities of researchers to shape materials on the nanoscale have enabled significant and rapid growth in the development of new nanomaterials-based applications and technologies. The controlled synthesis of metal and metal oxide nanoparticles in the quantum size domain is at the forefront of nanomaterials research due to the fact that the properties of nanoscale materials (e.g. electronic, optical, mechanical, chemical and magnetic properties) not only differ significantly from those of bulk materials, but they become critically dependent on particle size, shape, surface chemistry and inter-particle interactions (Grassian, V. H. J., Phys. Chem. C, 2008, 112, 18303-18313). Metallic silver (Ag) nanoparticles (NPs), in particular, have found use in a broad range of applications such as catalysis (Eising, R., et al., Langmuir, 2011, 50, 9893-9897), electronics (Li, Y. N., et al., J. Am. Chem. Soc., 2005, 127, 3266-3267), biosensing (Zhou, W., Int. J. Nanomedicine, 2011, 6, 381-386), water treatment (Pradeep, T. and Anshup, Thin Solid Films, 2009, 517, 6441-6478), and medicine (Jain, P. K., et al., Acc. Chem. Res., 2008, 41, 1578-1586).

While the antibacterial effects of silver species (in particular, ionic silver) have been known for centuries, in recent years there has been renewed interest in silver in the form of Ag NPs for applications in health care and medicine. This interest is due in part to increasing bacterial resistance to classical antibiotics (Rai, M. K., et al., J. Appl. Microbiol., 2012, 112, 841-852). Ag NPs offer novel modes of action and target different cellular structures compared with existing antibiotics, and have vastly increased reactivity over ionic silver, based on equivalent silver mass content, as a result of their large surface area to volume ratios. Several areas of medical care have already benefitted from the ongoing development of Ag NP-based materials. Applications include Ag NP-based wound dressings (Fong, J. and Wood, F., Int. J. Nanomedicine, 2006, 1, 441-449), Ag NP-based biomaterials for orthopaedics, such as use in artificial joint replacement and bone prostheses (Ren, N., et al., J. Mater. Chem., 2012, 22, 19151-19160), Ag NPs as bactericidal coatings for medical devices (Roe, D., et al., J. Antimicrob. Chemotherapy, 2008, 61, 869-876), and Ag NP incorporation into dental materials (US 2007/0213460).

Silver has a long history of use in preventative dentistry. For instance, silver nitrate ($AgNO_3$) and diamine silver fluoride ($Ag(NH_3)_2F$), often referred to simply as AgF, have been used to prevent or arrest carious lesions. However, a recognised undesirable side effect of these products is that they stain tooth structure and tooth-coloured restorations (Knight, G. M., et al., Aust. Dent. J., 2005, 50, 242-245). Suspensions of Ag NP-based materials may offer a unique solution to this problem, as they are non-staining, but have the potential to deliver enhanced antibacterial effects.

The antimicrobial activity of Ag NPs is known to be critically dependent on the dimensions of the particles. Specifically, many studies have revealed that smaller sized particles impart greater antimicrobial activity, on the basis of equivalent silver mass content (Morones, J. R., et al., Nanotechnology, 2005, 16, 2346-2353, and Guzman, M., et al., Nanomed.-Nanotech. Biol. Med., 2012, 8, 37-45)). The origin of this apparent size-dependent effect has been the subject of much investigation, and there are several commonly cited explanations. The first is that under aerobic conditions, Ag NPs of smaller size exert increased bacterial toxicity as a result of increased availability of $Ag^+$ ions on the surface of the particles, due to their higher specific surface areas when compared to larger sized particles. While the specific mechanism of bactericidal action of $Ag^+$ ions is currently not fully understood, it is thought to be related to the inactivation of critical thiol-containing enzymes upon cellular interaction. Additionally, $Ag^+$ is believed to detrimentally affect the replication of DNA in cells treated with $AgNO_3$. Furthermore, experimental evidence has also shown that ionic silver from both Ag NP and $AgNO_3$ sources causes structural and morphological changes in treated cells. The second explanation for the observed particle size dependence of Ag NP antibacterial activity is based on reports of a size-dependent interaction of Ag NPs with bacteria.

The consequence of these key findings is that recently there has been significant emphasis on designing synthetic routes that enable a high level of control over Ag NP size, size distribution and stability in suspension (i.e. no increase in size due to particle aggregation). Many methods have been investigated for the size-controlled synthesis of silver nanoparticles, including electrochemical methods, thermal decomposition, laser ablation, microwave irradiation, sonochemical approaches, and chemical reduction methods.

The chemical reduction method for metal NP synthesis is well-studied and can be carried out under mild conditions. This synthetic approach can be tailored to enable the rational design and development of more advanced functional nanocomposite materials. This typically involves solution-phase chemical reduction of a metal salt and precipitation of the particles within a continuous solvent matrix, forming a colloidal sol. This process is commonly performed in the presence of stabilising molecules (e.g. surfactants, lipids, polymers) in order to prevent unwanted aggregation of nanocrystals, and to control the growth, size and shape of the particles, as well as impart some control over their surface chemistry, functionality and dispersibility in a specific solvent system.

Beyond their role as stabilisers, surfactants and amphiphilic polymers can also act as structure-directing agents and templates. For instance, when present in solution at the time of metal salt reduction, they can direct the growth of nanocrystals and influence the resulting NP morphology by stimulating anisotropic growth and the preparation of faceted NPs of defined, non-spherical shapes (Wiley, B. J., et al., J. Phys. Chem. B, 2006, 110, 15666-15675, and Murphy, C. J., et al., Mrs Bulletin, 2005, 30, 349-355). Furthermore, under certain conditions, these molecules can undergo cooperative association to form various colloidal aggregate structures including micelles, bilayers and vesicles, which can subsequently be used as soft templates for NP synthesis. This strategy is increasingly being used to control the size, size distribution and morphology of individual NPs, as well as the larger NP-containing structures. In a template-based NP synthesis, the outer surface of the colloidal aggregate is typically used to accumulate and sequester synthetic precursors, most commonly metal salts, where they are subsequently chemically reduced, thereby initiating nucleation and growth.

Ionic surfactant micelles form an important class of NP templating structures, as their inherent surface charge imparts colloidal stability, and facilitates surface adsorption of the precursors via electrostatic interactions. A critical property of surfactant solutions is the critical micelle concentration (cmc). This is a property which is known to change significantly for ionic surfactants upon the addition of electrolytes. The form of the surfactant molecules (monomer vs. aggregated), and thus the morphology of the template, critically depends on whether the surfactant concentration used during NP synthesis is above or below the cmc of the surfactant in the presence of the corresponding metal salt.

If the ionic surfactant molecules are present in solution as monomers, then a micellar form of the template structure ceases to exist. To ensure the formation of uniform ionic micelle templates for NP synthesis, the surfactant concentration must be in excess of the cmc (adjusted to account for the presence of a metal salt), but less than the critical concentration which causes a change in shape of the spherical micelles. A template that is uniform in terms of size, shape and surface characteristics is necessary to synthesise nanoscale materials with consistent properties and behavior.

Dental caries is caused by bacterial processes that lead to demineralisation of dental hard tissues resulting from the proton by-production of carbohydrate metabolism. Dental caries is a biofilm process comprising over 700 species of bacteria and archea possibilities which form on the tooth surface, with the colonisation community becoming more complex and the proportions of contributing bacteria changing as the disease progresses and cavitation develops. Historically, the dental profession has used a surgical "drill and fill" approach. Currently, in operative procedures, only significantly damaged carious tissue (infected dentine) is removed. Subjacent to this a further layer of affected dentine is usually retained where bacteria have invariably invaded the dentine tubules.

For placement of tooth coloured composite resin fillings, acid treatment with 37% phosphoric acid is used to demineralise enamel creating micro-porosities for attachment of adhesive resin microtags before the filling is applied. However, to achieve bonding to dentine, which has a much greater organic content, mild acid treatment is followed by application of bifunctional primer molecules, such as hydroxyethyl methacrylate (HEMA), to encourage formation of a hybrid layer within the collagen-mineral matrix. The hydrophilic end of the HEMA molecule interacts with collagen, while the hydrophobic end interacts with composite resin filling material to chemically bind the resin to the tooth. The alternative to composite, amalgam, does not require acid treatment or other sophisticated chemistry as it is merely placed as a space filler in the cavity and is only retained mechanically.

Treating the symptoms by merely cutting away the demineralised tissue, however, does not address the cause of the disease process, leaving the dentition vulnerable to further destruction by protons resulting from bacterial activity. Conventional filling materials do not target the bacterial source of the disease either. Instead, they simply seal the remaining bacteria within the tooth. This prevents decay until the seal provided by the filling is breached, causing re-activation of the bacteria and leading to a recurrence of the infection. Thus, in order to effectively eradicate dental caries, all remaining bacteria must be eliminated.

Applications for disinfecting tooth surfaces currently available include chemical regimes (chlorhexidine, fluoride, iodine, calcium hydroxide, zinc oxide eugenol (ZnOE), hypochlorites, EDTA, peroxide bleaching agents, Carisolv™, ozone) and laser irradiation. All in some way are ineffective, unable to penetrate tooth tissue, have undesirable side effects, or are not cost effective.

The applicant has found that there is a critical "cmc boundary" for systems comprising anionic surfactants and a metal salt precursor, and that this boundary governs the form of the surfactant molecules at a given concentration, and thus the NP template, and also directs the mechanism of formation of surfactant-Ag nanocomposite materials, and the morphology of the final nanostructures.

The applicant has further found that these materials are effective anti-bacterial agents, and that the anti-bacterial activity is greatly enhanced when bacteria are exposed to these materials in the presence of an electric field. The materials are therefore potentially useful for treating or preventing dental caries.

It is therefore an object of the invention to provide a novel material based on an assembly of surfactant-silver nanoparticle aggregates having a number of potential applications one of which is the treatment of bacterial infections, or to at least provide a useful alternative to existing materials.

SUMMARY OF THE INVENTION

In a first aspect of the invention there is provided an assembly of micelle aggregates, wherein each micelle aggregate comprises:
(i) micelles of an anionic surfactant, and
(ii) nano-sized particles of metallic silver (Ag),
wherein the assembly has at least one dimension in the range 100 to 1000 nm.

Examples of the anionic surfactant include salts of any one of the group comprising alkyl sulfates, alkyl ether sulfates, alkyl aryl ether sulfates, alkyl sulfonates, alpha-olefin sulfonates, alkylbenzene sulfonates, alkyl sulfoacetates, alkyl sulfosuccinates, alkyl phosphates, alkyl ether phosphates, alkyl carboxylates, alkyl ether carboxylates, and phosphate esters. In some embodiments of the invention the surfactant is a salt of an alkyl sulfate, for example sodium dodecyl sulfate (SDS), the salt of an alkylbenzene sulfonate, for example sodium dodecylbenzene sulfonate (SDBS), the salt of an alkyl ether sulfate, for example sodium lauryl ether sulfate (SLES), or the salt of an alkyl sulfate, for example ammonium lauryl sulfate (ALS).

In some embodiments of the invention the at least one dimension is in the range 200 to 800 nm, for example in the range 300 to 600 nm.

The micelle aggregates may be of any suitable size, and in some embodiments have a diameter in the range of approximately 50 to 70 nm.

In some embodiments of the invention the micelles each have a diameter in the range 3 to 10 nm, for example approximately 5 nm.

In some embodiments the nano-sized particles of Ag have a diameter in the range 8 to 10 nm.

In some embodiments the nano-sized particles of Ag are spherical.

In a second aspect of the invention there is provided a product in the form of an aqueous dispersion of assemblies of the invention, or in the form of a powder or granules containing assemblies of the invention.

In a third aspect of the invention there is provided a method for preparing an assembly of the invention, comprising the steps:
 (i) contacting an aqueous solution of an anionic surfactant having a concentration in the range 0.5 to 7.5 mM with an aqueous solution of a Ag salt such that the molar ratio of the anionic surfactant to Ag salt is in the range 0.08 to 12.5, and
 (ii) adding a reducing agent to reduce the Ag salt to metallic Ag.

Any suitable water soluble Ag salt may be used, but the preferred Ag salt is $AgNO_3$. Alternative Ag salts include $AgNO_2$ and $CH_3COOAg$.

The reducing agent may be selected from any group of suitable reducing agents. The preferred reducing agent is $NaBH_4$.

The concentration of the anionic surfactant may be in the range 2 to 6 mM.

In a further aspect of the invention there is provided a use of an assembly of the invention for the treatment or prevention of a bacterial infection.

The bacterial infection may be an infection caused by any bacteria including, but not limited to, gram positive bacteria, such as *Staphylococcus oxford*, *Streptococcus mutans*, *Streptococcus mitis*, *Streptococcus gordonii*, *Enterococcus faecalis*, or gram negative bacteria, such as *Pseudomonas aeruginosa*, or *Escherichia coli*.

In a further aspect of the invention there is provided a product for use in the treatment or prevention of a bacterial infection, which product comprises assemblies of micelle aggregates, wherein each micelle aggregate comprises:
 (i) micelles of an anionic surfactant, and
 (ii) nano-sized particles of metallic silver (Ag), wherein the assemblies have at least one dimension in the range 100 to 1000 nm.

In yet a further aspect of the invention there is provided a method of treating or preventing a bacterial infection in teeth comprising applying an aqueous dispersion of an assembly of the invention to the teeth of a patient.

In some embodiments the aqueous dispersion is applied to at least partially coat the surface of one or more teeth of the patient, and an electric current is applied on or near to the coated surface of the one or more teeth. The electric current is typically in the range 0.5 to 1.0 mA at 1 to 10 V.

DETAILED DESCRIPTION

Figure 1:
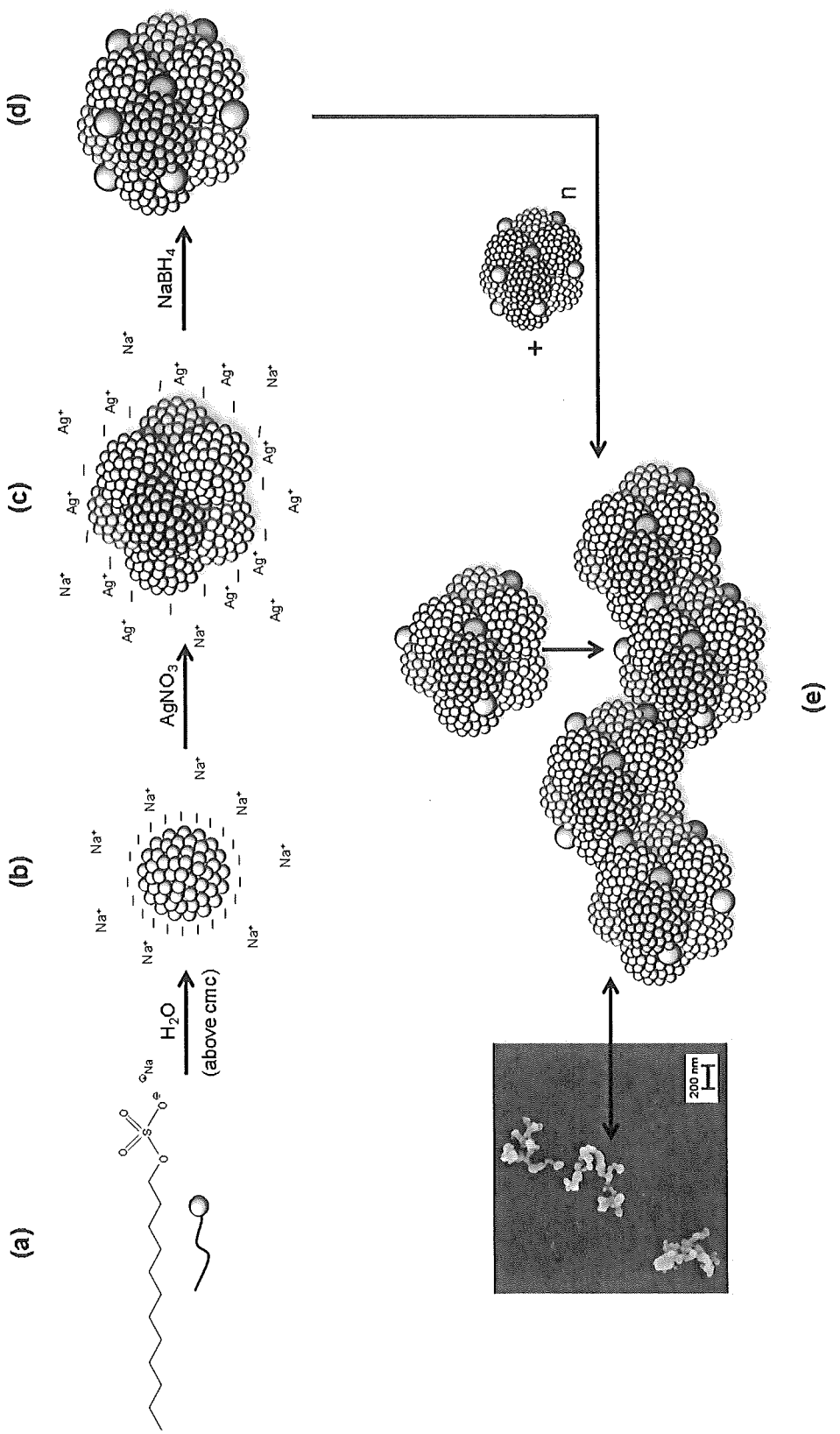
FIG. 1 shows a proposed mechanism for the preparation of Ag NP-containing SDS micelle aggregate assemblies.

The assembly of the invention is an aggregation of molecular aggregates and associated metallic silver nanoparticles. The molecular aggregates are aggregations of surfactant molecules. The surfactant is an anionic surfactant, and the silver particles are in the nano-size range.

The invention is based upon the finding that such assemblies can be formed in a manner where solid material contained within the assemblies, and aqueous dispersions of these discrete assemblies, are more or less uniform in terms of the size and structure of the assemblies. In contrast, existing combinations of surfactant micelles and silver particles comprise multiple structures exhibiting varied degrees of micelle aggregation and incorporation of silver particles, leading to quite different physical and chemical properties. The assembly structure of the invention, being prepared in a careful and controlled manner, allows for a high degree of physical structure uniformity and consequentially useful characteristics considered desirable in applications such as microbial control.

The term "anionic surfactant" means an amphiphilic surfactant molecule or molecules having both hydrophobic and hydrophilic moieties where the hydrophobic moiety consists of a hydrocarbon tail and the hydrophilic moiety consists of a negatively charged head group.

The term "critical micelle concentration" means the surfactant concentration above which micelles of that surfactant can spontaneously form.

The term "effective critical micelle concentration" relates to a system comprising both an ionic surfactant and a metal salt, and means the surfactant concentration above which micelles of that surfactant can spontaneously form at a given metal salt concentration.

The term "nano-" or "nano-sized" means having at least one size, dimension or scale in the nanometer range, typically several nanometers to several hundred nanometers. A nanoparticle (NP) is therefore any particle having at least one dimension, e.g. diameter, in the range of several nanometers to several hundred nanometers. A nanocomposite (NC) is any composite of materials comprising particles where the particles have at least one dimension in the range of several nanometers to several hundred nanometers.

The term "molecular aggregate" means a collection or self-association of surfactant molecules in a cluster (micelle) with their hydrophobic hydrocarbon tails located in the interior of the micelle and their head groups forming a hydrophilic exterior surface.

The term "micelle aggregate" means a self-assembled structure formed from a group of molecular aggregates (micelles).

The term "assembly" means a grouping of micelle aggregates and surface-bound silver nanoparticles.

The term "alkyl" means any hydrocarbon moiety including whether branched or straight chained and whether saturated or unsaturated.

The term "aryl" means any moiety comprising at least one aromatic ring.

The invention is described below in detail with reference to the anionic surfactant sodium dodecyl sulfate (SDS), but it will be appreciated that the invention is applicable to a wide range of anionic surfactants including alkylbenzene sulfonates (e.g. sodium dodecylbenzenesulfonate (SDBS)), alkyl ether sulfates (e.g. sodium lauryl ether sulfate (SLES)) and alkyl sulfates (e.g. ammonium lauryl sulfate (ALS)).

It has been recognised by the applicant that the effective critical micelle concentration ($cmc_{eff}$) of a surfactant-metal salt system significantly impacts on the form of surfactant molecules and thus the template for the formation of nanoparticles (NPs). In particular, the $cmc_{eff}$ for the SDS/AgNO$_3$, SDBS/AgNO$_3$, SLES/AgNO$_3$, ALS/AgNO$_3$ and SDS/CH$_3$COOAg systems have been identified.

The addition of electrolytes to pure ionic surfactant solutions (such as during a chemical reduction-type nanoparticle synthesis) has significant implications with regard to i) molecular aggregation and the formation of micelles (i.e. cmc value), and ii) inter-particle interactions and aggregation behavior of pre-formed micelles. It is well known that the addition of an electrolyte to an ionic surfactant solution decreases the cmc from that of the pure surfactant. This is a result of a decrease in the electrostatic repulsion between the charged head groups of the amphiphilic surfactant molecules, making the formation of micellar structures more energetically favorable and resulting in the formation of micelles at lower surfactant concentration.

The effect of numerous electrolytes on the cmc of ionic surfactants has been investigated in the past, but these studies have not explored the use of the relevant metal salts for nanoparticle synthesis, despite the fact that surfactant-metal salt systems are common for the synthesis of metal and metal oxide nanoparticles.

As shown in Example 1, the addition of AgNO$_3$ to aqueous SDS solutions at 25° C. results in a decrease in the cmc of the pure surfactant (8.1 mM). The addition 0.6-8.8 mM AgNO$_3$ resulted in lower cmc values ranging from 7.4-4.6 mM, with the extent of lowering typical for that caused by univalent counterions. The decrease in cmc is thought to be a result of increased screening by the Ag$^+$ cations of the electrostatic repulsion between the negatively charged sulfate head groups of the SDS molecules, making the formation of aggregate structures more energetically favorable, thus resulting in the formation of micelles at a lower SDS concentration.

Example 2 was conducted to determine the cmc values for additional surfactant-AgNO$_3$ systems. The cmc of pure SDBS, SLES and ALS at 25° C. was determined to be 1.4, 3.1 and 6.7 mM, respectively. During the process of $cmc_{eff}$ determination for these surfactants (and concurrent antimicrobial testing, see Example 6), it became readily apparent that it was not necessary to perform conductivity measurements at every AgNO$_3$ concentration tested for SDS (Example 1) in order to verify a similar extent of decrease in the surfactant cmc upon the addition of AgNO$_3$ or to subsequently estimate the effective cmc boundary for each new surfactant.

The SDS template takes the form of 50-70 nm aggregates of SDS micelles, with the specific aggregate size dependent on the initial AgNO$_3$ concentration. The positively charged Ag$^+$ counter ions are adsorbed to the negatively charged sulfate groups at the SDS micelle aggregate surface ($\zeta$=−59.8 mV, pH=6) via electrostatic interactions. The addition of a reducing agent, such as NaBH$_4$, leads to the chemical reduction of the Ag$^+$ ions, resulting in the formation and growth of monodisperse 6.7-9.2 nm Ag NPs (FIG. 6, Table 1) at the surface of the SDS micelle aggregates.

Figure 6:
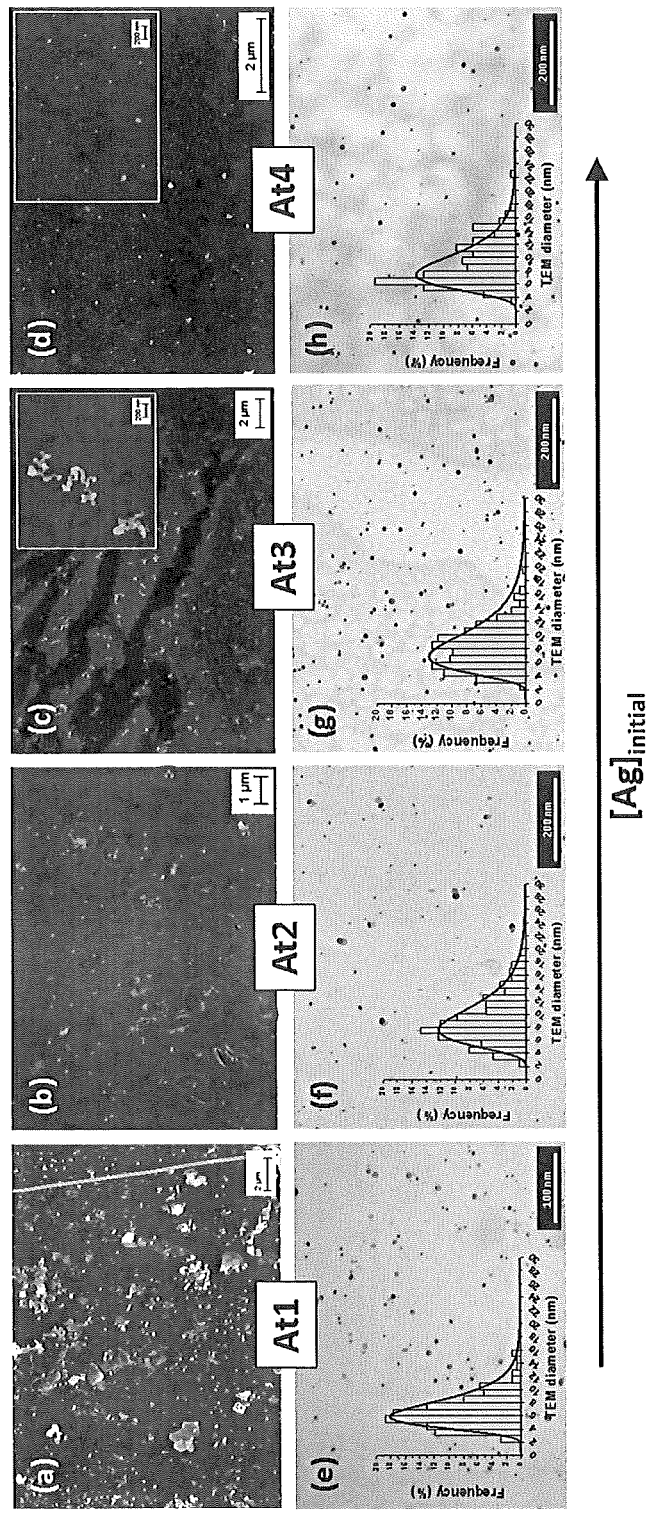
FIG. 6 shows SEM micrographs ((a) to (d)) for samples At1-At4 (with expanded views inset) and TEM micrographs ((e) to (h)) for samples At1-At4 (with particle size distribution histograms).

TEM and SEM analyses were carried out on samples At1, At2, At3 and At4, and representative micrographs are shown in FIG. 6. These four samples were all prepared at the $cmc_{eff}$, but the initial silver concentration ranged from 0.6-8.8 mM (65-949 μg mL$^{-1}$). TEM images (FIG. 6, bottom panels) show the presence of electron dense Ag NPs only, and in all cases, regardless of $[Ag]_{initial}$, the micrographs show fairly monodisperse, spherical nanoparticles, evenly distributed across the grid. The average particle diameter for each sample prepared at the $cmc_{eff}$ is <10 nm (ranging from 6.7-9.2 nm), and all are within one standard deviation of each other. Thus, $[Ag]_{initial}$ was shown not to significantly affect the size or dispersity of the primary Ag NPs when the SDS-Ag NC materials were prepared at the $cmc_{eff}$.

Conversely, however, the morphology of the assembled Ag NP-containing SDS micelle aggregate structures prepared at the $cmc_{eff}$, which are visible in SEM micrographs (FIG. 6, top panels) is highly dependent on $[Ag]_{initial}$. Sample At1 ($[Ag]_{initial}$=0.6 mM, 65 μg mL$^{-1}$) necessarily had a high SDS/AgNO$_3$ molar ratio in order to maintain the sample at the $cmc_{eff}$ (12.4; Table 2). This large excess of SDS led to drying artefacts when the sample was prepared for SEM analysis, and the morphology of the structures shown in FIG. 6(a) cannot be considered representative of the morphology of the suspended structures in sample At1. The final silver concentration of this sample, as determined by inductively coupled plasma-mass spectrometry (ICP-MS), was $[Ag]_{final,ICP-MS}$=35.5 μg mL$^{-1}$.

SEM micrographs of sample At2 ($[Ag]_{initial}$=2.9 mM, 313 μg mL$^{-1}$) revealed the presence of a large number of SDS micelle aggregates in the range of ~60 nm, as well as some larger micelle assembly structures (circled, FIG. 6(b)). The final silver concentration of this sample, as determined by ICP-MS, was $[Ag]_{final,ICP-MS}$=52.6 μg mL$^{-1}$, a silver concentration higher than sample At1, as expected. The 9.2 nm silver nanoparticles clearly visible in the TEM micrographs of the same sample (FIG. 6(f)) were not visible in any of the SEM images.

SEM analysis of sample At3 ($[Ag]_{initial}$=5.9 mM, 636 μg mL$^{-1}$) indicated that the sample was primarily composed of fairly uniformly-sized assembly structures of SDS micelle aggregates (FIG. 6(c)). Again, the 8.7 nm dispersed Ag NPs visible in TEM micrographs (FIG. 6(g)) were not visible in SEM images obtained for the same sample. The final silver concentration of this sample, as determined by ICP-MS was $[Ag]_{final,ICP-MS}$=63.9 μg mL$^{-1}$, higher than samples At1 and At2, as expected.

SEM images of sample At4 ($[Ag]_{initial}$=8.8 mM, 949 μg mL$^{-1}$) revealed a notable absence of SDS micelle assembly structures. Instead, only single spherical structures were visible (FIG. 6(d)), consistent with SDS aggregate structures in the range of ~70 nm. Dispersed Ag NPs clearly visible in TEM images were not visible in any of the SEM micrographs. The final silver concentration of this sample, as determined by ICP-MS was $[Ag]_{final}$=33.1 μg mL$^{-1}$, the lowest silver concentration of any of the samples prepared at the $cmc_{eff}$ (At1-At4).

The average diameters obtained from TEM analysis ($D_{TEM}$) and DLS measurements ($D_{DLS}$) for each SDS-Ag NC sample prepared at the $cmc_{eff}$ are shown in Table 1. The high polydispersity index values (>0.45) obtained from DLS measurements for samples At1-At3 are indicative of polydisperse suspensions, and indeed, multimodal size distributions were observed. Diameters obtained from DLS measurements are not necessarily the true dimension of the dispersed particles of interest; rather, the diameter obtained by this technique (the hydrodynamic diameter) is the diameter of a sphere diffusing at the same rate as the particles. Thus, the non-spherical conformation of the Ag NP-containing SDS micelle assembly structures in samples At1-At3 affects the interpretation of their diffusion speed, which is reflected in the high PDI values. Sample At4, however, was found to be relatively monodisperse with a low PDI value <0.20. This is in agreement with the monodisperse, spherical structures observed in the corresponding SEM micrographs (FIG. 6(d)).

TABLE 1

Average TEM diameter ($D_{TEM}$) with associated standard deviation and DLS diameter ($D_{DLS}$) with associated polydispersity index (PDI) of SDS-Ag NC materials prepared at $cmc_{eff}$.

| Sample | $D_{TEM}$ nm (s.d.) | $D_{DLS}$ nm (PDI) |
|---|---|---|
| At1 | 6.7 (2.7) | 2225 (1.000) |
| At2 | 9.2 (4.1) | 1106 (1.000) |
| At3 | 8.7 (4.2) | 396 (0.474) |
| At4 | 8.6 (3.4) | 96.4 (0.192) |

FIG. 1 shows the steps involved in the preparation of Ag NP-containing SDS micelle aggregate assemblies (SDS-Ag NC materials) when an SDS concentration at or above the $cmc_{eff}$ is used:

(a) the structure of SDS (top), and its representation as an amphiphilic surfactant molecule with a hydrophilic head group, represented by a sphere, and hydrophobic aliphatic tail (bottom);

(b) representation of a spherical, dissociated SDS micelle with a negative surface charge formed upon the addition of water at concentrations above the cmc;

(c) representative arrangement of counter-ions around the anionic surfactant micelle upon addition of $AgNO_3$;

(d) reduction of $Ag^+$ ions by $NaBH_4$, and depiction of the association of resulting Ag NPs at the surface of an SDS micelle aggregate; and (e) an assembly of Ag NP-containing SDS micelle aggregates with assembly driven by the high surface energy of uncoated Ag NPs.

The predominantly uncoated Ag NPs formed at the aggregate surface inherently have a high surface energy. This likely drives a secondary aggregation process, in which the SDS micelle aggregates containing surface-bound Ag NPs assemble together in order to reduce the overall surface energy of the entire nanocomposite assembly. The extent of assembly is dependent on the number of accumulation sites for $Ag^+$ ions, and the amount of $Ag^+$ cations present in solution, i.e. the molar ratio of $SDS/AgNO_3$.

There are several benefits of fabricating such SDS-Ag NP assembly structures. For example, the immobilisation of Ag NPs on the surface of SDS micelle aggregates prevents aggregation of individual Ag NPs, and establishes a well-defined spatial distribution of Ag NPs. This provides a potential route to novel materials with tunable collective properties, while still maintaining the size-dependent properties of the individual nanoparticles, for example their antibacterial character. The ability to sequester a large number of Ag NPs within an SDS micelle aggregate assembly structure may be beneficial for accumulated Ag NP delivery in biomedical applications, particularly considering the known biocompatible nature of SDS. The highly negative surface charge of the resulting Ag NP-containing nanoassemblies also offers potential for further surface functionalisation, for example through electrostatic interactions or layer-by-layer deposition of functional or responsive polyelectrolytes.

The assembly of the invention has at least one dimension in the range 100 to 1000 nm. Each assembly may be of irregular shape and so the dimension may be length, width, diameter, circumference, or any other measurable size dimension. In general terms, the assembly has a "size", or more precisely "at least one dimension", in the range 100 to 1000 nm. The size of each assembly may be any subset range including, but not limited to, 200 to 900, 200 to 800, 300 to 800, 300 to 600, 400 to 700, 500 to 600, or any combination of these lower and upper limits. It should also be appreciated that the individual assemblies of a product or bulk material comprising the assemblies may have different sizes falling within any of the above ranges.

It should be noted that assemblies of micelles of an anionic surfactant and Ag NPs that fall outside the size range of 100 to 1000 nm are unlikely to form. Since the micelle aggregates typically have a diameter in the range 50 to 70 nm, an assembly of such aggregates would have at least one dimension of around 100 nm or greater. Assemblies having a size greater than 1000 nm are unlikely to remain dispersed in suspension and therefore they will be short-lived and unstable.

Although the invention is described in detail with reference to the alkyl sulfate salt SDS, any one of a wide range of anionic surfactants may be used including salts of any one of the group comprising alkyl sulfates (e.g. ALS), alkyl ether sulfates (e.g. SLES), alkyl aryl ether sulfates, alkyl sulfonates, alpha-olefin sulfonates, alkylbenzene sulfonates (e.g. SDBS), alkyl sulfoacetates, alkyl sulfosuccinates, alkyl phosphates, alkyl ether phosphates, alkyl carboxylates, alkyl ether carboxylates, and phosphate esters.

The micelles of the invention have a diameter in the range 3 to 10 nm. But it should be appreciated that in certain embodiments of the invention the diameter range may be 4 to 9, 4 to 8, 4 to 7, or 4 to 6 nm. In one embodiment, the diameter is approximately 5 nm.

The nano-sized particles of Ag may have any size suitable for the formation of the assembly of the invention. The diameter of the Ag particles is typically in the range 8 to 10 nm, but may fall within a broader range, for example 5 to 10 nm or even 5 to 15 nm.

When preparing the assemblies of the invention, the molar ratio of anionic surfactant to Ag salt is important. The molar ratio may be any ratio in the range 0.08 to 12.5, or any range in between including, but not limited to, 0.1 to 11.0, 0.2 to 10.0, 0.3 to 9.0, 0.4 to 8.0, 0.5 to 7.0, 1.0 to 6.0, 2.0 to 5.0, or 3.0 to 4.0. In the case of SDS, the molar ratio is preferably in the range 0.5 to 12.5. In the case of SDBS, the molar ratio is preferably in the range 0.1 to 2.0. In the case of SLES, the molar ratio is preferably in the range 0.6 to 3.5. In the case of ALS, the molar ratio is preferably in the range 6.5 to 8.5.

The assembly of the invention may have many potential uses. One such use is the treatment or prevention of bacterial infections. This is demonstrated in Example 5. Sample At3 was tested against a representative range of microorganisms associated with the oral environment, including both Gram-positive and Gram-negative bacteria. Silver determinations from repeated samples of sample At3 indicated that an effective concentration between 42 and 63 µg mL$^{-1}$ was achieved. Furthermore, when diluted with water, sample At3 proved to be strongly antibacterial against *Streptococcus gordonii* at up to 1:50 dilutions, against *Escherichia coli*, *Streptococcus mutans* and *Streptococcus mitis* at up to 1:10 dilutions, and against *Staphylococcus oxford* at up to 1:5 dilutions. However, sample At3 was unable to consistently prevent growth when tested against cultures of *Enterococcus faecalis*, a pathogenic organism associated with resistant dental root canal infections. Zones of reduced growth were, however, observed for *E. faecalis* when exposed to neat At3, but when diluted in a 6 mM solution of SDS, reduced growth was evident at up to 1:20 dilutions. *S. mutans* and *S. oxford* were even more effective, at up to 1:50 dilutions, when the At3 sample applied was diluted with a 6 mM solution of SDS. Results from the in vitro assay developed to test the influence of electric current on bacterial growth of *E. coli* (see Example 1) indicated the potential of an antibacterial effect with sample At3 at dilutions down to 1:50 against *E. faecalis* when an electric current is applied.

Both gram-positive and gram-negative bacteria displayed reduced viability when exposed to electric current alone (see Example 6). *S. mutans*, which is a gram-positive, appeared more susceptible to electric current compared to the gram-negative *E. coli* and *P. aeruginosa*. Viability of *S. mutans* decreased to less than 50% after 30 seconds of electric current exposure. By comparison, both *E. coli* and *P. aeruginosa* showed less than 50% of loss of viability after 120 seconds exposure to electric current. The exposure of bacteria to sample At3 in the presence of an electric current resulted in less than 10% of bacteria remaining viable after 60 seconds. Thus, the use of iontophoresis to apply an electric field on a tooth as a means of driving charged Ag NP-containing micelle assembly structures deep into dentine has the additional benefit of antimicrobial enhancement.

It should be noted that the combination of current and voltage used for the in vitro assay of Example 6 differs in magnitude to that anticipated necessary for application to teeth clinically due to the vast difference in resistance to passage of an electric field presented by the human body. Anticipated parameters necessary for clinical use are based on known parameters for the delivery of fluoride by iontophoresis (0.4 to 1.0 mA/cm$^2$, 1 to 9 volts) and other silver formulations (1.0 mA). It is generally regarded that doses below 1.0 mA are safe for pulp tissue without detrimentally affecting viability.

One potential use of a product based on the assembly of the invention is the treatment of dental caries. For cavitated caries lesions, the product can be applied to teeth after conventional surgical caries removal (partial or complete removal of infected dentine using drill, air abrasion, laser or chemomechanical means) to disinfect the dentine tubules and provide a residual reservoir of Ag-NPs to confer ongoing resistance to reinfection. Iontophoresis may be used to enhance the antimicrobial activity of the Ag-NPs and to transport Ag-NPs down dentine tubules to reach bacteria known to advance ahead of the infected, demineralised zone of lesions.

The product of the invention can also be used as a cavity toilet to disinfect tooth preparations made on sound tooth structure such as when preparing for indirect cast restorations (inlays, onlays, crowns and bridgework). Iontophoresis is used to enhance penetration into areas of exposed dentine.

Non-cavitated caries lesions are managed preventively without surgical intervention as it is recognised that demineralised lesions are capable of remineralisation in the presence of appropriate reservoirs of calcium, fluoride and phosphate ions provided the surface remains grossly intact without frank cavitation. For non-cavitated caries lesions, the product of the invention may be applied to teeth to disinfect the lesion, eliminating bacteria associated with the lesion and binding to enamel. Enamel almost completely comprises hydroxyapatite mineral, with a much lower organic component. Enamel is the most dense structure of the human body, with densely packed, aligned prismatic assemblies of hydroxyapatite crystals, and aprismatic randomly orientated hydroxyapatite crystals in regions of tooth surface exposed to particularly high functional load such as cusp tips. The dense structure of enamel, and absence of tubules such as are found in dentine, means that iontophoresis is not able to achieve deep penetration of Ag-NP through enamel surfaces, but nevertheless will enhance the antimicrobial activity of Ag-NP greatly, and will ensure that penetration into porous non-cavitated enamel surfaces is optimised.

The assembly of the invention can be formulated in any suitable manner appropriate for its use. A typical formulation is an aqueous colloidal dispersion, but may also be prepared in solid form, for example as a powder, for later dispersion or suspension in water or any other suitable liquid carrier. When diluted to a suitable concentration, the dispersion in water normally appears to be a transparent, colourless and odorless liquid. The product may be light sensitive, and should be stored appropriately, for example in the dark or in amber coloured vials.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

The invention is further described with reference to the following examples. It will be appreciated that the invention as claimed is not intended to be limited in any way by these examples.

EXAMPLES

Example 1

Determination of cmc$_{eff}$ of SDS in the Presence of AgNO$_3$

Figure 2:
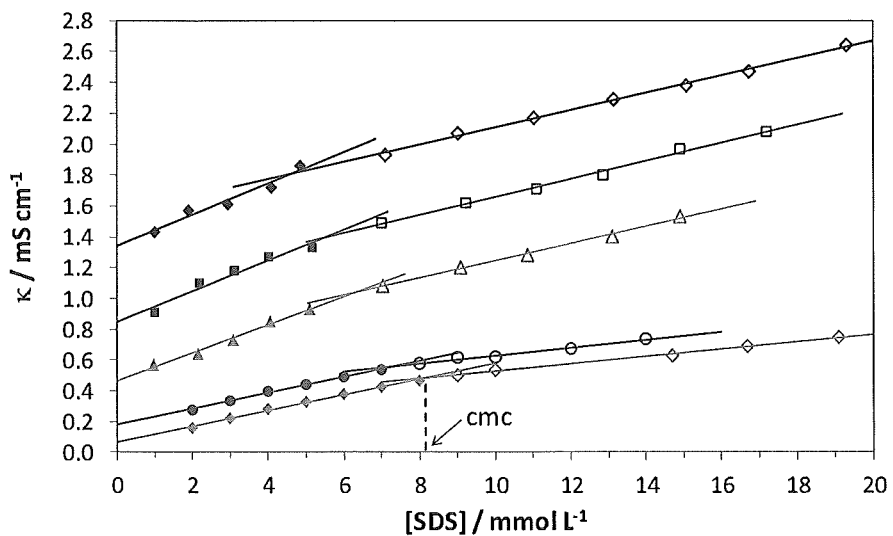
FIG. 2 shows electrical conductivity as a function of SDS concentration for 5 SDS solutions.
Figure 3:
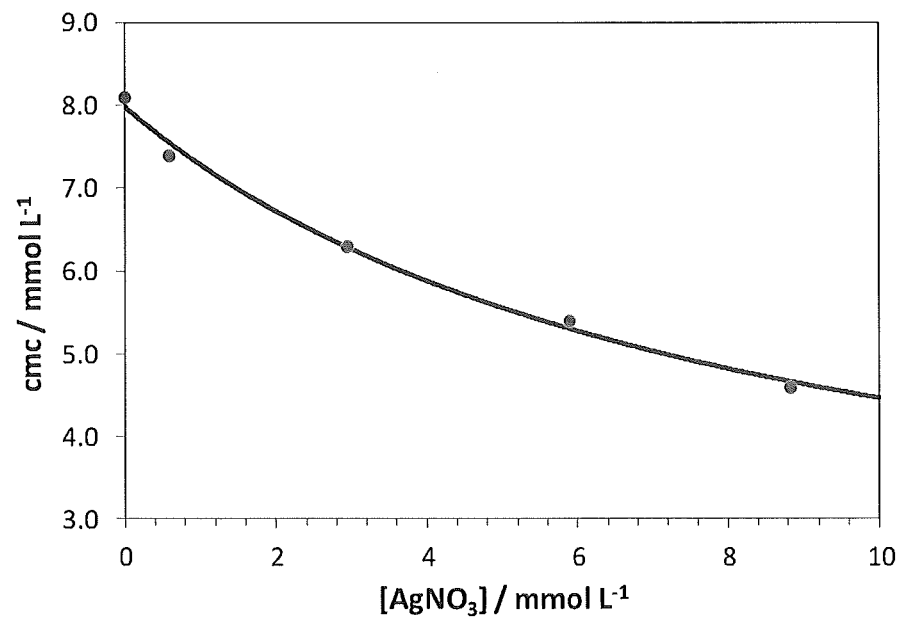
FIG. 3 shows the effect of $AgNO_3$ concentration on the cmc of SDS.

Electrical conductivity measurements (mS cm$^{-1}$) were performed on five SDS solutions over a range of concentrations, with each solution containing a different amount of added AgNO$_3$. FIG. 2 shows electrical conductivity (κ) as a function of SDS concentration recorded at 25° C. for 5 samples containing 0 mg (◇), 10 mg (○), 50 mg (△), 100 mg (□) and 150 mg (◊) AgNO$_3$, corresponding to 0, 0.6, 2.9, 5.9 and 8.8 mM AgNO$_3$, respectively. Standard deviations for each data point are <0.014 mS cm$^{-1}$ in all cases. Closed symbols represent the data points used for the linear regression analysis below the cmc, and the open symbols for the analysis above the cmc. For each sample, regardless of the electrolyte content, as the SDS concentration was varied, an inflection point in the electrical conductivity was observed, indicating the cmc. A linear regression analysis of the conductivity data of each of the five samples was performed above and below the inflection point. In all cases, no significant deviations from linearity were observed over the concentration ranges. A dashed line has been added to one data set to indicate the point of intersection of the two corresponding linear equations, thus indicating the cmc. The cmc of pure SDS in $H_2O$ in the absence of $AgNO_3$ was determined to be 8.1 mM. The effect of $AgNO_3$ concentration on the cmc of SDS in $H_2O$ at 25° C. is shown in FIG. 3. The curve represents a critical 'cmc boundary' for the SDS/$AgNO_3$ system, i.e. the $cmc_{eff}$ of SDS at a given $AgNO_3$ concentration between 0-10 mM.

Example 2

Determination of $cmc_{eff}$ of SDBS, SLES and ALS in the Presence of $AgNO_3$

Following the procedure detailed in Example 1, electrical conductivity measurements were performed on sodium dodecylbenzenesulfonate (SDBS), sodium lauryl ether sulfate (SLES) and ammonium lauryl sulfate (ALS) solutions containing different amounts of added $AgNO_3$ in order to determine the $cmc_{eff}$ of each surfactant. In each case, an inflection point was observed in the data when the electrical conductivity was plotted as a function of surfactant concentration, indicating the cmc. Linear regression analysis was performed as described in Example 1. The resulting $cmc_{eff}$ values for SDBS, SLES and ALS are shown in Table 2. The cmc of pure SDBS, SLES and ALS at 25° C. was determined to be 1.4, 3.1 and 6.7 mM, respectively.

TABLE 2

Experimentally-determined $cmc_{eff}$ values for SDBS, SLES and ALS in $H_2O$ at 25° C. at various $AgNO_3$ concentrations.

| [$AgNO_3$] mM | $Cmc_{eff}$ of SDBS mM | $Cmc_{eff}$ of SLES mM | $Cmc_{eff}$ of ALS mM |
|---|---|---|---|
| 0 | 1.4 | 3.1 | 6.7 |
| 0.6 | 1.2 | 2.1 | 4.6 |
| 2.9 | 0.7 | 1.9 | |
| 5.9 | 0.5 | | |

Example 3

Preparation of SDS-Ag NC Materials and the Effect of $cmc_{eff}$

Figure 4:
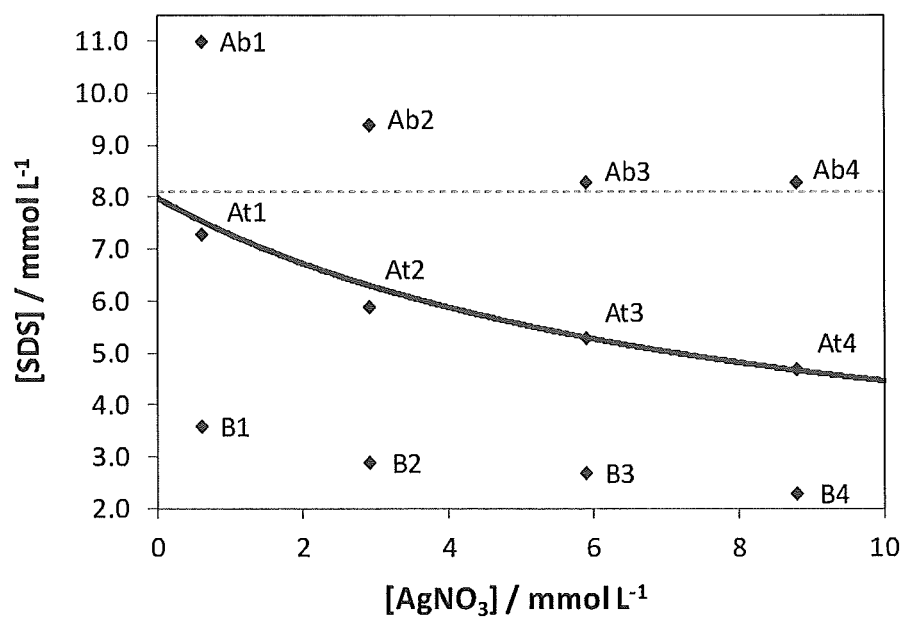
FIG. 4 shows the SDS and $AgNO_3$ concentrations of samples and their relationship to the $cmc_{eff}$ boundary.

In this experiment, 12 different SDS/$AgNO_3$ combinations were selected for use in the synthesis of SDS-Ag NC materials: 4 samples were prepared using an SDS concentration below the $cmc_{eff}$ (B1-B4), 4 samples were prepared using an SDS concentration at the $cmc_{eff}$ (At1-At4), and 4 samples were prepared with an SDS concentration above the $cmc_{eff}$ (Ab1-Ab4). FIG. 4 shows the SDS and $AgNO_3$ concentrations used in the synthesis of the samples. Notably, their relationship to the $cmc_{eff}$ boundary, shown as a solid line, can be observed. The dotted grey line represents the cmc of pure SDS in the absence of any $AgNO_3$.

All glassware used in the preparation of SDS-Ag NC materials was acid washed in a bath of freshly prepared aqua regia (3:1 HCl:$HNO_3$), thoroughly washed with DI $H_2O$, then dried before use. An appropriate amount of SDS was completely dissolved in 100 mL DI $H_2O$ to give a desired concentration within the range of 2.3-11 mM (see Table 3). This concentration range spans a wide range of concentrations which fall both above and below the cmc of pure SDS in water, in the absence of any salts (known to be between 8.0-8.3 mM). Silver nitrate (0.06-0.88 mmol) was then added with stirring to the SDS solutions so that the molar ratio of SDS to $AgNO_3$ ranged from 0.3-18.6 (see Table 3). A small volume of the SDS solution was used to dissolve the solid electrolyte and transfer it to the reaction vessel.

For 4 of the samples (At1-At4), immediately prior to reduction of $AgNO_3$ with $NaBH_4$, a small volume (1.2 mL) was transferred to 12 mm square polystyrene sizing cuvettes for dynamic light scattering (DLS) measurements. DLS measurements were also performed on a simple aqueous suspension of SDS micelles in the absence of $AgNO_3$ for comparison. The hydrodynamic diameter of SDS micelles in $H_2O$ could not be determined by DLS measurements due to the fact that the size of the micelles is below the practical limit of detection. However, upon addition of $AgNO_3$ to SDS micelle suspensions resulting in a molar ratio at the $cmc_{eff}$, DLS results indicate the presence of larger, monodisperse aggregate structures with diameters ranging from 52.5-68.4 nm. In fact, a systematic increase in Z-Avg was observed with an increase in the initial silver concentration. These structures can be assumed to be aggregates of small SDS micelles, with aggregation induced as a result of a decrease in the thickness of the electrical double layer upon $AgNO_3$ addition. The SDS micelle aggregates appear as relatively spherical structures in SEM micrographs, and also appear in the micrographs to be around 50-70 nm in diameter. These aggregate structures are considered to be those that form the templates for Ag NP synthesis at SDS concentrations at or above the $cmc_{eff}$.

For the reduction of $Ag^+$ ions to $Ag^0$, 1 mL of a freshly prepared $NaBH_4$ solution (1:1 molar ratio $AgNO_3$:$NaBH_4$) was added drop-wise with stirring to the $Ag^+$-containing SDS solution. Upon addition of $NaBH_4$, the colour immediately changed from a cloudy whitish colour to a dark brown colour, indicating the successful reduction of $Ag^+$ ions to $Ag^0$ and the formation of colloidal Ag nanoparticles. The mixture was covered and allowed to stir in the dark for 30 min at room temperature, then centrifuged at 10,000 rpm for 30 min. The yellow-coloured supernatant was collected, and retained for characterisation, and antibacterial and iontophoresis studies.

All of the resulting aqueous suspensions of SDS-Ag NC materials appeared yellow in colour, which is consistent with the presence of monodisperse Ag NPs. This visual observation was confirmed by UV-Vis spectrophotometric analysis of the suspensions. In all cases, a single surface plasmon absorption peak was observed in the range of 390-402 nm, a range which is characteristic of the presence of nanocrystalline spherical silver nanoparticles, and consistent with Mie theory for spherical particles. The wavelength corresponding to the absorption maximum of the surface plasmon resonance (SPR) band is highly sensitive to the size and dielectric properties of the Ag NPs, and is known to red-shift to longer wavelengths upon aggregation. The absence of any systematic band shift and the narrow full band widths at half maximum (FWHM) together indicate that all of the SDS-Ag NC suspensions in the series contain monodisperse, small, spherical Ag NPs of approximately the same size, regardless of the SDS/$AgNO_3$ ratio used during synthesis, and regardless of whether the preparation occurred using a ratio below, at or above the $cmc_{eff}$.

TABLE 3

Concentrations and molar ratios of SDS surfactant and AgNO$_3$ for SDS-Ag NC preparations.

| Sample | [SDS] (mmol L$^{-1}$) | [AgNO$_3$] (mmol L$^{-1}$) | SDS/AgNO$_3$ molar ratio |
|---|---|---|---|
| Ab1 | 11 | 0.6 | 18.6 |
| Ab2 | 9.4 | 2.9 | 3.2 |
| Ab3 | 8.3 | 5.9 | 1.4 |
| Ab4 | 8.3 | 8.8 | 0.9 |
| At1 | 7.3 | 0.6 | 12.4 |
| At2 | 5.9 | 2.9 | 2.0 |
| At3 | 5.3 | 5.9 | 0.9 |
| At4 | 4.7 | 8.8 | 0.5 |
| B1 | 3.6 | 0.6 | 6.2 |
| B2 | 2.9 | 2.9 | 1.0 |
| B3 | 2.7 | 5.9 | 0.5 |
| B4 | 2.3 | 8.8 | 0.3 |

Example 4

Preparation of Surfactant-Ag NC Materials at cmc$_{eff}$

This example was designed to demonstrate that alternative surfactants could be used to replace SDS in the preparation of surfactant-stabilised Ag NC materials. SDBS, SLES and ALS were used at concentrations at their respective cmc$_{eff}$ values to prepare aqueous suspensions of SDBS-, SLES-, and ALS-Ag NC materials. In this case, 6 different surfactant/AgNO$_3$ combinations were selected for use in the synthesis of the materials: 3 samples were prepared using SDBS/AgNO$_3$ at cmc$_{eff}$, with [Ag]$_{initial}$=0.6, 2.9 and 5.9 mM; 2 samples were prepared using SLES/AgNO$_3$ at cmc$_{eff}$, with [Ag]$_{initial}$=0.6 and 2.9 mM; 1 sample was prepared using ALS/AgNO$_3$ at cmc$_{eff}$, with [Ag]$_{initial}$=0.6 mM. All of the resulting aqueous suspensions of surfactant-Ag NC materials again appeared yellow in colour, as described in Example 3. Surfactant/AgNO$_3$ molar ratios for these samples ranged from 0.08 to 7.6.

Example 5

Electron Microscopy of SDS-Ag NC Materials: Role of cmc$_{eff}$

Figure 5:
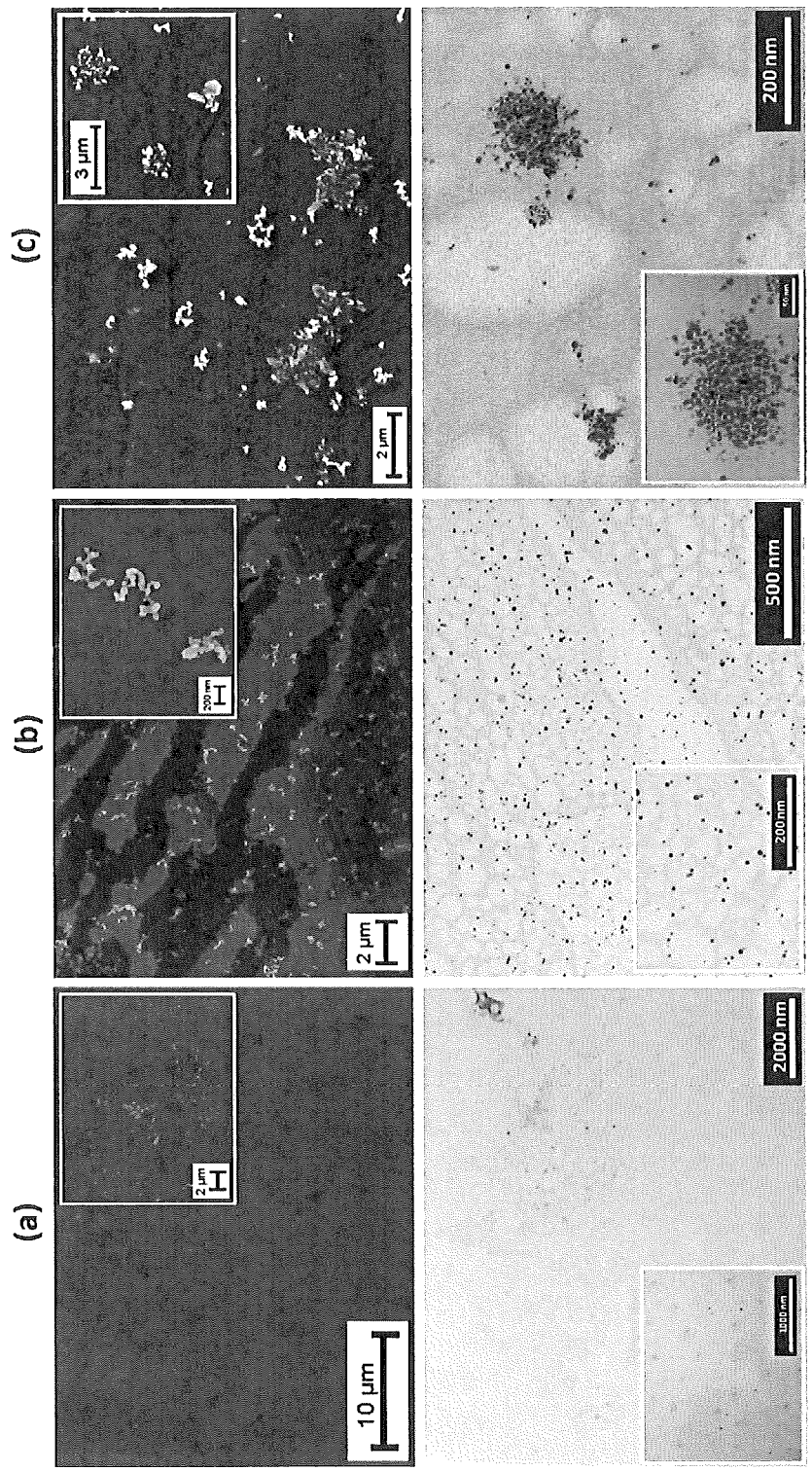
FIG. 5 shows representative SEM and TEM micrographs for samples B3, At3 and Ab3.

In order to further investigate the role of the cmc$_{eff}$ in the preparation of SDS-Ag NC materials, TEM and SEM analyses were carried out on samples B3, At3 and Ab3. Representative micrographs are shown in FIG. 5. These three samples were prepared with equivalent silver concentrations ([Ag]$_{initial}$=5.9 mM or 636 µg mL$^{-1}$), but a controlled variation in SDS concentration placed each of these samples in different regimes: below, at or above the cmc$_{eff}$.

Considering first sample B3, SEM micrographs (FIG. 5(a), top) revealed a notable absence of aggregated SDS micelles as previously observed in FIG. 4. This is not surprising, however, as the samples were prepared below both the standard, and the effective, cmc of SDS. TEM micrographs from the same sample (FIG. 5(a), bottom) revealed a small number of small, spherical silver nanoparticles in the range of ~8-10 nm (estimated). A statistically relevant number of particles could not be obtained for particle size determination. ICP-MS analysis revealed a final, extremely low silver concentration of 1.2 µg mL$^{-1}$ for this sample.

For sample At3, SEM micrographs (FIG. 5(b), top) clearly show fairly uniformly-sized assemblies of SDS micelle aggregates. TEM analysis of the same sample (FIG. 5(b), bottom) showed the presence of small, monodisperse, spherical nanoparticles well dispersed across the grid. A statistical sample of the particle size was obtained by direct measurement of the diameters of more than 250 particles. From these measurements, a particle size distribution histogram was prepared. The distribution was fitted successfully with a model for a lognormal size distribution, yielding an average diameter, d, of d=8.7 nm and a standard deviation, σ, of σ=4.2 nm. Silver nanoparticles of this size were too small for detection with the SEM instrumentation used, which is why they cannot be observed in the corresponding SEM micrograph for sample At3. ICP-MS analysis revealed a final silver concentration of 63.9 µg mL$^{-1}$ for this sample.

Lastly, considering the electron microscopy analysis of sample Ab3 (FIG. 5(c)), both SEM and TEM micrographs show a notable presence of polydisperse, aggregated structures. TEM analysis revealed large, dense aggregates of Ag NPs, and SEM analysis revealed what appeared to be uncontrolled, random assemblies of SDS micelle aggregates and non-uniform structures. The final silver concentration of this sample was 32.5 µg mL$^{-1}$, as determined by ICP-MS.

Example 6

Effect of SDS-Ag NC Materials on Gram-Positive and Gram-Negative Bacteria

Antimicrobial activities for SDS-Ag NC suspensions were tested against a range of microorganisms, including both Gram-positive organisms (*Staphylococcus oxford, Streptococcus mutans, Streptococcus mitis, Streptococcus gordonii* and *Enterococcus faecalis*) and Gram-negative microorganisms (*Eschericia coli* and *Pseudomonas aeruginosa*).

Pure stock cultures of *S. mutans* (UAB159), *S. mitis* (ILB), *S. gordonii* (DL1), *E. faecalis* (JH22), *S. oxford*, *P. aeruginosa* (OTIS), and *E. coli* (DH5α) were obtained from the Department of Oral Sciences, University of Otago, Dunedin, New Zealand. Colonies of *S. mutans, S. mitis, S. gordonii*, and *E. faecalis* were anaerobically grown on Columbia sheep-blood agar (Fort Richard Laboratories Ltd., Auckland, New Zealand) at 37° C. for 24 hours. *S. oxford, P. aeruginosa* and *E. coli* were grown on trypticase soy agar (TSB) (Fort Richard Laboratories Ltd., Auckland, NZ) at 37° C. for 24 hours under aerobic conditions. Colonies grown on these plates were subcultured weekly to inoculate TSB broths, incubated at 37° C. for 24 hours, from which experimental TSB plates were streaked to generate monoculture lawns of growth for antimicrobial testing of colloidal SDS-Ag NC products. The agar well diffusion assay was used to obtain standard zones of inhibition, which were measured. This technique was originally developed for testing topical antimicrobial agents to treat infected burn wounds in patients. Bacteria were directly exposed to the colloidal SDS-Ag NP samples at a range of concentrations (1.0 to 65 µg mL$^{-1}$), then incubated at 37° C. for 24 hours. Antimicrobial activity of solutions of pure SDS and pure AgNO$_3$ were tested under the same conditions against the same range of microorganisms.

Figure 7:
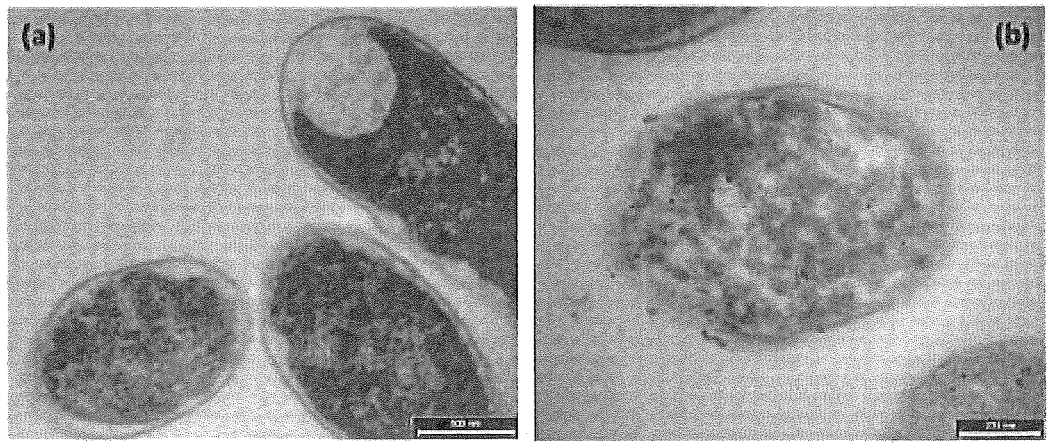
FIG. 7 shows TEM micrographs of *E. coli* cells: (a) untreated cells (unstained), scale bar=500 nm; (b) treated with sample At3 (unstained), scale bar=200 nm.

Transmission electron microscopy was used to investigate the morphological changes that occur to *E. coli* and *S. mutans* following treatment with Sample At3. Results are shown in FIGS. 7 (*E. coli*) and 8 (*S. mutans*).

To prepare the bacteria cells for the study, cells cultured in TSB broth were treated with 500 µL of colloidal SDS-Ag NC sample At3 at a silver concentration of 63.9 µg mL$^{-1}$, as determined by ICP-MS. The broth was transferred to 15 mL Falcon tubes and centrifuged at 1500 rpm for 5 min to pelletise the cells. The treated cells were then reconstituted with 2.5% glutaraldehyde in 0.1 M sodium cacodylate buffer, and allowed to fix for 2 hours. The cells were repeatedly centrifuged and washed in 0.1 M sodium cacodylate buffer for 5 min, three times. Cells were exposed post-fixing to 2% OsO$_4$ in 0.1 M sodium cacodylate buffer for 12 hours at 4° C., then 2 hours at room temperature for a further 2 hours. The cells were again repeatedly centrifuged and washed in 0.1 M sodium cacodylate buffer for 5 min, three times. Finally, the cells were mixed with an equal volume of liquid 3% low-melting agarose and placed at 4° C. for 15 min to set. The resulting gel was sectioned before dehydrating using a sequence of ethanol solutions at increasing concentration (50%, 70%, 95%, 100%×2) before resin infiltrating (1:1 EtOH:resin, 1:2 EtOH:resin, 100% resin ×5). Sections were embedded in a silicone mould and sectioned into 80 nm slices using a Reichert-Jung Ultracut E ultramicrotome (C. Reichart A G, Vienna, Austria), and placed on a formvar-coated copper slot grid, contrasted with an LKB 2168 Ultrostain grid stainer (LKB-Produckter AB, Bromma, Sweden). Digital images were captured using a Philips CM100 BioTWIN transmission electron microscope [TEM] (Phillips/FEI Corporation, Eindhoven, Holland) fitted with a MegaView III digital camera (Olympus Soft Imaging Solutions GmbH, Münster, Germany).

Further broth cultures were subjected to the same protocol but omitting the steps involving fixing or staining with OsO$_4$, after finding that this better revealed the presence of colloidal SDS-Ag NCs. The uptake of Ag NPs by *E. coli* bacteria cells can be recognised by the dense coating of black particles observed over the outer cell membrane surface (FIG. 7(*b*)). Gram-negative bacteria, such as *E. coli*, have only a thin (~2-3 nm) peptidoglycan layer between the cytoplasmic membrane and the outer membrane. The Ag NPs appear to interact with the bacterial membrane of *E. Coli* and cause damage to the cell through membrane disruption. Interestingly, the Ag NPs appear to remain dispersed, even upon interaction with Gram-negative bacteria, as there is no evidence of aggregated Ag NPs in the TEM micrographs. This result suggests that the aggregated SDS micelles provide sufficient stabilisation of individual Ag NPs, up to the point of interaction with a Gram-negative bacteria membrane.

Figure 8:
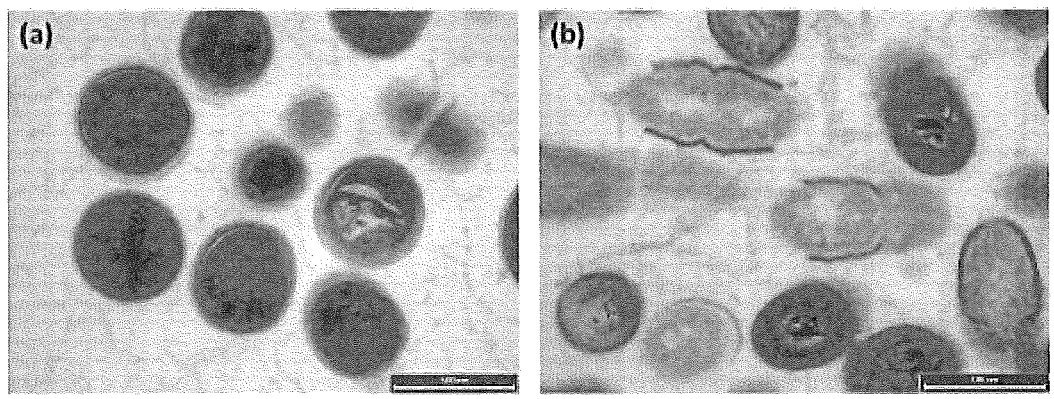
FIG. 8 shows TEM micrographs of *S. mutans* cells: (a) untreated cells (stained), scale bar=500 nm; (b) treated with sample At3 (stained), scale bar=500 nm.

Gram-positive bacteria, such as *S. mutans*, have a thicker (30 nm) peptidoglycan cell wall, compared to Gram-negative bacteria, but lack an outer membrane. Treatment of Gram-positive bacteria with sample At3 resulted in a bactericidal effect, with TEM images showing lysis of *S. mutans* cells (FIG. 8(*b*)). It should be noted that while Ag NPs are clearly detectable only at the edge of the cell, this may be due to the dark osmium stain granules filling the cell and obscuring the detection of Ag NPs in the TEM micrograph.

Following the same procedure, antibacterial activities for SDBS-, SLS- and ALS-Ag NC suspensions were also tested against the same organisms. Zones of inhibition, coupled with re-streaking, were measured to provide non-quantitative relative determinations of activity. The results are shown in Table 4.

TABLE 4

Anti-bacterial activity of surfactant-A.

| Organism | SDS | SDBS | SLES | ALS |
|---|---|---|---|---|
| *P. aeruginosa* | strong | strong | strong | strong |
| *E. coli* | strong | weak | none | none |
| *E. faecalis* | v. strong | v. weak | weak | weak |
| *S. oxford* | v. strong | strong | weak | weak |
| *S. mutans* | v. strong | strong | weak | strong |
| *S. mitis* | v. strong | strong | weak | weak |
| *S. gordonii* | v. strong | strong | weak | weak |

Example 7

Effect of Electric Current on Bacteria

An in vitro model was developed to investigate the influence of electric current on the antimicrobial properties of At3. Using the same bacteria selected for earlier experiments, Streptococci and Enterococci were grown on Columbia sheep-blood agar, *S. oxford* and *E. coli* were grown on trypticase soy agar. These cultures were used to inoculate broths of brain-heart infusion (BHI) which were incubated at 37° C. for 24 hours aerobically before harvesting by centrifugation, washing three times in phosphate-buffered saline (PBS) and resuspending bacterial cells to a concentration of ~2×10$^9$ CFU mL$^{-1}$. Washed bacteria were diluted to approximately 2×10$^8$ CFU mL$^{-1}$ in suspension, and maintained on ice while an electric current was applied. At 30 second intervals 100 µL samples were recovered, serially diluted and spot-plated (50 µL) onto TSB agar. Following appropriate incubation, colonies were enumerated to determine the surviving bacteria.

A combination of 3.2 A, 2.5V killed 1 mL of both Gram-positive and Gram-negative bacteria in a time-dependent manner, and in combination with At3 significantly improved the antimicrobial activity against *E. coli* compared to the action of At3 alone. The number of *E. coli* decreased proportionally to the duration of current applied. After 90 sec, bacterial colony numbers decreased to <50% of the starting population. By 120 sec, around 70% of the bacteria were killed. *P. aeruginosa* showed a more gradual decrease in viability and had the highest number of viable colonies remaining (49%) compared to other microorganisms after exposure to 120 sec of direct current. Both *S. gordonii* and *S. mitis* showed a steady state declination curve when exposed to electric current. However, the standard deviation for *S. mitis* remained high compared to other microorganisms. It took 120 sec to decrease the viable colonies of *S. gordonii* to <50%, while *S. mitis, S. oxford* and *E. faecalis* had colony populations <50% after exposure to electric current for only 90 sec. For *S. oxford*, the number of viable colonies started to decrease after 60 sec of exposure to electric current, and dramatically decreased to <50% at 90 sec. *S. mutans* decreased to less than 50% of viable colonies after exposure to 30 sec of electric current. After 60 sec, there were less than 10% of viable colonies and no colonies remained after exposure to 120 sec of current.

Example 8

Effect of Electric Current on *E. coli* Concurrently Exposed to SDS-Ag NCs

Sample At3 was used to test the effect of electrical current combined with SDS-Ag NCs on viability of the microorganism *E. coli*. In the absence of current, sample At3 alone caused a reduction in the number of viable colonies. Specifically, application of 30 µL of sample At3 ([Ag]$_{final}$=63.9 µg mL$^{-1}$) reduced the number of viable colonies to ~63% after a delay of 120 sec (an equivalent time period over which an electrical current would be applied). Notably, when combined with exposure to electrical current, 1 µL of a 1:50 dilution of sample At3 ([Ag]=1.3 µg mL$^{-1}$) was sufficient to decrease the number of viable colonies to ~10% after 120 seconds. Increasing the volume of the diluted version of sample At3 used to 5 µL, and again combining sample At3 with electrical current exposure, <10% of viable colonies were detected after 60 sec.

Example 9

Interaction of SDS-Ag NCs with Hydroxyapatite and Gelatin

Sample At3 was applied to pure hydroxyapatite (HAp; $Ca_{10}(PO_4)_6(OH)_2$) and gelatin (partially hydrolysed collagen), being representative of the chemical composition for both the inorganic and organic portions of the tooth tissue as a whole.

In a similar approach to evaluating interactions of silver diamine fluoride with hydroxyapatite and protein, 2.5 g of powdered high resolution hydroxyapatite (Calbiochem, Merck KGaA, Darmstadt, Germany) was exposed to 500 µL of sample At3 for 48 h in a tumbler at room temperature. Following exposure of sample At3, treated HAP was washed with deionised water and centrifuged four times, before drying. Following each centrifugation (1000 rpm, 10 min), the resulting supernatants were tested for antimicrobial activity, according to the method of Example 5.

0.1 g of gelatin from porcine skin (Sigma Aldrich Co., St Louis, USA) prepared in 4 mL of distilled water was exposed to 500 µL of sample At3 for 48 hrs in a tumbler at room temperature. Following exposure sample At3, treated gelatin was washed with deionised water and centrifuged four times, before dried. Following each centrifugation (1000 rpm, 10 min), the resulting supernatants were tested for antimicrobial activity, according to the method of Example 5.

For both HAP and gelatin, different specimens were exposed to sample At3 under laboratory fluorescent lighting, and where the specimens were protected from light. Dried HAP and gelatin were carbon coated and analysed by SEM and TEM. Energy dispersive X-ray analysis (EDS) was used to verify the presence of silver. SEM analysis revealed a very high affinity for the SDS-Ag NC assemblies to remain bound to gelatin discs and HAp crystals, despite repeated washing and centrifuging cycles. The presence of Ag on HAp treated with sample At3 was confirmed by EDS. These results indicate that sample At3 will bind efficiently to tooth tissue.

Example 10

Interaction of SDS-Ag NCs with Tooth Structure

Category A ethics approval was gained from the University of Otago, Dunedin, New Zealand to conduct in vitro studies involving the application of colloidal SDS-Ag NC products on extracted human teeth. Freshly extracted human teeth with intact crown morphology, free of previous restorations or clinical signs of developmental abnormalities (such as hypoplasia, fluorotic defects, congenital defects or tetracycline staining) were collected. Following extraction, the teeth were immediately rinsed removing gross surface debris and loose tags of supporting periodontal tissues. Each tooth was immersed in a 1% sodium hypochlorite solution (Milton disinfectant) at 4° C. for 24 hours, rinsed with saline, before transfer into Hanks' Balanced Salt Solution (HBSS) to which thymol crystals were added to confer antibacterial properties, for long-term storage at 4° C. Teeth were randomly assigned to different treatment regimes. For each tooth, 2 mm (w)×1 mm (h)×2 mm (d) cavities were prepared on the mesial and distal mid-proximal surface of the crown using a high-speed air turbine handpiece (KaVo Powertorque lux 646B; KaVo, Biberarch, Germany) with a green stripe, coarse grit (151 µm) cylindrical diamond friction grip bur (Komet 836.314.012, Komet, Rock Hill, S.C., USA), exposing dentine at the inner portion of the cavities. In some cases, smear layer removal was attempted using 37% phosphoric acid applied to dentine for 15 sec. For teeth with dental caries, cavities were not prepared mechanically, and the carious lesion surface was treated.

Sample At3 (10 µL) was applied to both sound and carious teeth with and without the smear layer removed. Several application strategies were investigated. In some cases, the sample was applied to the tooth using a laboratory micropipette, and in others, using a dental applicator Microbrush® (Microbrush® International, Grafton, USA). The sample was allowed to remain on the tooth for either 30 or 60 sec, before washing off. Treated teeth were embedded in Struers Epofix resin (Streurs, Ballerup, Denmark), sectioned into 500 µm slices longitudinally with an automated cutting machine (Streurs Accutom-50) using an aluminium oxide cut-off disc (Streurs 357CA, Cat. No. 40000045), before mounting the tooth sections on ceramic base plates, and polishing with automated rotary grinding and polishing machines (Struers Tegra-Pol-21 & Tegra-Force-5) prior to carbon coating for SEM analysis. The polishing sequence involved using increasingly fine aluminium oxide polishing papers (500, 1200, 2400 and 4000 grits) for 5 min each, followed by increasingly fine diamond suspension polishing pastes (Struers DP 9 µm, 6 µm, 3 µm and 1 µm pastes with Struers DP lubricant for 5 min each applied to magnetic adhesive polishing discs (Struers MD-Plan and Streurs MD-Dur) on a Struers MD-Disc fixed to the Streuers Tegra-Pol-21 for 5 min each. Following each polishing step, specimens were ultrasonically cleaned in distilled water for 3 min prior to the next stage.

Polished sections were carbon coated with an Emitech K575X Peltier-cooled high-resolution sputter coater (EM Technologies Ltd, Kent, England) fitted with an Emitech 250X carbon coater. Specimens were examined on a Cambridge 360 SEM (Cambridge Instruments, Cambridge, UK) fitted with a Dindima Image Slave frame grabber (Dindima Group Pty Ltd, Ringwood, Vic, Australia), or on a JEOL field emission FE-SEM 6700 (JEOL Ltd, Tokyo, Japan) fitted with a JEOL 2300F energy dispersive x-ray spectroscopy (EDS) system (JEOL Ltd, Tokyo, Japan).

SEM images of prepared sections of sound teeth treated with sample At3 showed bright spots indicating the presence of Ag NP-containing SDS micelle assemblies. EDS analysis of these spots positively confirmed the presence of silver. The sizes of the bright spots appear to be in the range of 150-250 nm, which suggests that the integrity of the assembled nanostructures is preserved upon diffusion in teeth.

When the smear layer was left in place during treatment with sample At3, many Ag-containing structures were seen to be present in the smear layer, but not on the tooth surface.

The application of phosphoric acid (37° A)) to dentine prior to the addition of sample At3 onto the tooth (using a microbrush, 30 sec) resulted in partial removal of the smear layer, with smear tags lifted out of the dentine tubules, thus exposing open tubules. Once the smear layer was removed, however, the Ag-containing structures were observed on/in dentine with good depth of penetration, ranging from ~2-72 μm.

Sample At3 (10 μL) was also applied to carious teeth, with partially demineralised dentine. A pipette was used to apply the sample which was left on the lesion surface for 60 sec, after which unadhered material was washed off. The Ag-containing nanostructures adhered well to partially demineralised dentine (caries lesions). Application of 37% phosphoric acid to carious teeth for 15 sec removes grossly demineralised tissue with severely denatured protein content, but does not remove all of the carious tissue. The tissue that remains, however, creates an appropriate interface for Ag-nanocomposite application.

Figure 9:
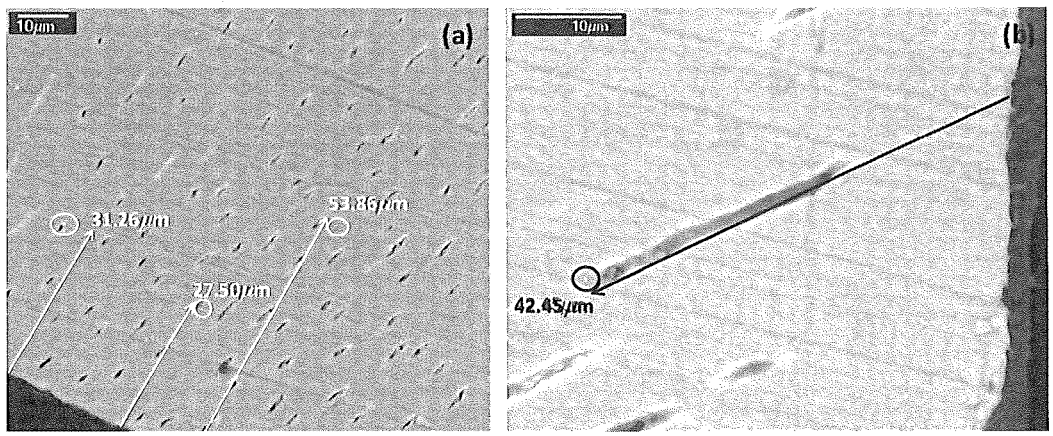
FIG. 9 shows SEM micrographs of sound tooth upon treatment with sample At3 (smear layer removed).

Finally, cavities were prepared exposing dentine on non-carious teeth. A 10 μL volume of sample At3 was applied to the cut dentine surface for 1 min, followed by a regimen of repeated washing with deionised water. Subsequently the teeth were sectioned for SEM and EDS examination (FIG. 9) revealing that the Ag NP-containing structures could bind to dentine with a strong affinity, penetrating up to 70 μM into dentine tubules unassisted, leaving a high density of silver nanostructures coating the sectioned tooth surface.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. An assembly of micelle aggregates, wherein:
   (i) each micelle aggregate comprises micelles of an anionic surfactant;
   (ii) the assembly comprises nano-sized particles of metallic silver (Ag) bound to a surface of the assembly; and
   (iii) the assembly has at least one dimension in the range of 100 to 1000 nm;
   wherein the assembly comprises a grouping of micelle aggregates.

2. The assembly as claimed in claim 1, wherein the anionic surfactant is a salt selected from the group consisting of alkyl sulfates, alkyl ether sulfates, alkyl aryl ether sulfates, alkyl sulfonates, alpha-olefin sulfonates, alkylbenzene sulfonates, alkyl sulfoacetates, alkyl sulfosuccinates, alkyl phosphates, alkyl ether phosphates, alkyl ether carboxylates, and phosphate esters.

3. The assembly as claimed in claim 1, wherein the anionic surfactant is a salt of an alkyl sulphate.

4. The assembly as claimed in claim 1, wherein the anionic surfactant is sodium dodecyl sulphate.

5. The assembly as claimed in claim 1, wherein the at least one dimension is in the range of 200 to 800 nm.

6. The assembly as claimed in claim 1, wherein the micelle aggregates have a diameter in the range of 50 to 70 nm.

7. The assembly as claimed in claim 1, wherein the micelles each have a diameter in the range of 3 to 10 nm.

8. The assembly as claimed in claim 1, wherein the nano-sized particles of Ag have a diameter in the range of 8 to 10 nm.

9. The assembly as claimed in claim 1, wherein the nano-sized particles of Ag are spherical.

10. A method for preparing the assembly of micelle aggregates defined in claim 1, comprising:
    (i) contacting an aqueous solution of an anionic surfactant having a concentration in the range of 0.5 to 7.5 mM with an aqueous solution of a Ag salt such that the molar ratio of the anionic surfactant to Ag salt is in the range of 0.08 to 12.5, and
    (ii) adding a reducing agent to reduce the Ag salt to metallic Ag.

11. The method as claimed in claim 10, wherein the Ag salt is $AgNO_3$, $AgNO_2$, or $CH_3COOAg$.

12. The method as claimed in claim 10, wherein the reducing agent is $NaBH_4$.

13. The method as claimed in claim 10, wherein the concentration of the anionic surfactant is in the range of 2 to 6 mM.

14. A method of treating or preventing a bacterial infection in teeth comprising applying an aqueous dispersion of the assembly of micelle aggregates as defined in claim 1 to the teeth of a patient.

15. The method as claimed in claim 14, wherein the aqueous dispersion is applied to at least partially coat the surface of one or more teeth of the patient, and an electric current is applied on or near to the coated surface of the one or more teeth.

16. The method as claimed in claim 15, wherein the voltage of the electric current is in the range of 0.5 to 1.0 mA at 1 to 10 V.

* * * * *